United States Patent
Wurziger et al.

(10) Patent No.: US 6,852,900 B2
(45) Date of Patent: Feb. 8, 2005

(54) METHOD FOR CARRYING OUT A METATHESIS REACTION OF UNSATURATED ORGANIC COMPOUNDS

(75) Inventors: Hanns Wurziger, Darmstadt (DE); Guido Pieper, Mannheim (DE); Norbert Schwesinger, Ilmenau (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 10/239,398

(22) PCT Filed: Mar. 1, 2001

(86) PCT No.: PCT/EP01/02301

§ 371 (c)(1),
(2), (4) Date: Jan. 14, 2003

(87) PCT Pub. No.: WO01/70387

PCT Pub. Date: Sep. 27, 2001

(65) Prior Publication Data

US 2003/0163011 A1 Aug. 28, 2003

(30) Foreign Application Priority Data

Mar. 23, 2000 (DE) ........................... 100 14 297

(51) Int. Cl.$^7$ ................................................ C07C 6/02
(52) U.S. Cl. ...................... 585/643; 585/646; 585/647
(58) Field of Search ................................ 585/643, 646, 585/647

(56) References Cited

U.S. PATENT DOCUMENTS 4,681,956 A * 7/1987 Schrock ........................ 556/12
5,803,600 A 9/1998 Schubert et al.

FOREIGN PATENT DOCUMENTS

| DE | 4433439 | 3/1996 |
|----|---------|--------|
| EP | 0456373 | 11/1991 |
| WO | WO 9951344 | 10/1999 |
| WO | WO 0051720 | 9/2000 |
| WO | WO 00/51720 | * 9/2000 |

* cited by examiner

*Primary Examiner*—Thuan Dinh Dang
(74) *Attorney, Agent, or Firm*—Millen White Zelano & Branigan, P.C.

(57) ABSTRACT

The present invention relates to a process for the metathesis reaction of unsaturated organic compounds.

14 Claims, No Drawings

METHOD FOR CARRYING OUT A METATHESIS REACTION OF UNSATURATED ORGANIC COMPOUNDS

The present invention relates to a process for the metathesis reaction of unsaturated organic compounds.

The metathesis reaction of suitable unsaturated organic compounds is a process which is carried out very frequently in the chemical industry and whose considerable importance is also reflected in numerous publications on this subject.

However, the performance of metathesis reactions on an industrial scale is accompanied by safety problems and dangers. Firstly, use is frequently made of relatively large amounts of highly toxic chemical substances, which in themselves already represent a considerable risk to people and the environment, and secondly the reaction conditions can in many cases only be controlled well with considerable effort. Furthermore, the achievement and maintenance of protective-gas conditions is often very complex in industrial-scale metathesis reactions of this type.

The object of the present invention is therefore to provide a process for the metathesis reaction of unsaturated organic compounds which avoids the above-mentioned disadvantages. In particular, It should be possible to carry out this process in a simple, reproducible manner with increased safety for humans and the environment and with good yields, the reaction conditions should be very easy to control, and the protective-gas conditions necessary for carrying out the reaction should be achievable without major technical effort.

This object is achieved, surprisingly, by the process according to the invention for the metathesis reaction of unsaturated organic compounds, in which at least one unsaturated organic compound in liquid or dissolved form is mixed with at least one metathesis catalyst in liquid or dissolved form in at least one microreactor and reacted for a residence time, and the organic compound formed is, if desired, isolated from the reaction mixture.

Advantage embodiments of the process according to the invention are described in the sub-claims.

In accordance with the invention, individual unsaturated organic compounds or mixtures of at least two of these compounds can be reacted by the claimed process. Preferably, individual unsaturated organic compounds are employed in the process according to the invention.

In a particularly preferred embodiment, the metathesis reaction is a ring-closing metathesis reaction of a single unsaturated organic compound.

For the purposes of the invention, a microreactor is a reactor having a volume of $\leq 1000\ \mu l$ in which the liquids and/or solutions are intimately mixed at least once. The volume of the reactor is preferably $\leq 100\ \mu l$, particularly preferably $\leq 50\ \mu l$.

The microreactor is preferably made from thin silicon structures connected to one another.

The microreactor is preferably a miniaturised flow reactor, particularly preferably a static micromixer. The microreactor is very particularly preferably a static micromixer as described in the patent application having the international publication number WO 96/30113, which is incorporated herein by way of reference and is regarded as part of the disclosure. A microreactor of this type has small channels in which liquids and/or chemical compounds in the form of solutions are mixed with one another by means of the kinetic energy of the flowing liquids and/or solutions.

The channels of the microreactor preferably have a diameter of from 10 to 1000 $\mu m$, particularly preferably from 20 to 800 $\mu m$ and very particularly preferably from 30 to 400 $\mu m$.

The liquids and/or solutions are preferably pumped into the microreactor in such a way that they flow through the latter at a flow rate of from 0.01 $\mu l/min$ to 100 ml/min, particularly preferably from 1 $\mu ml/min$ to 1 ml/min.

In accordance with the invention, the microreactor is preferably heatable.

In accordance with the invention, the microreactor is preferably connected via an outlet to at least one residence zone, preferably a capillary, particularly preferably a heatable capillary. After mixing in the microreactor, the liquids and/or solutions are fed into this residence zone or capillary in order to extend their residence time.

For the purposes of the invention, the residence time is the time between mixing of the starting materials and work-up of the resultant reaction solution for analysis or isolation of the desired product(s).

The residence time necessary in the process according to the invention depends on various parameters, such as, for example, the temperature or reactivity of the starting materials. It is possible for the person skilled in the art to match the residence time to these parameters and thus to achieve an optimum course of the reaction.

The residence time of the reaction solution in the system used comprising at least one microreactor and, if desired, a residence zone can be adjusted through the choice of the flow rate of the liquids and/or solutions employed. The reaction mixture is likewise preferably passed through two or more microreactors connected in series. This achieves an extension of the residence time, even at an increased flow rate, and the metathesis reaction components employed are reacted in such a way that an optimum product yield of the desired organic compound(s) is achieved.

In a further preferred embodiment, the reaction mixture is passed through two or more microreactors arranged in parallel in order to increase the throughput.

In another preferred embodiment of the process according to the invention, the number and arrangement of the channels in one or more microreactor(s) are varied in such a way that the residence time is extended, likewise resulting in an optimum yield of the desired organic compound(s) at the same time as an increased flow rate.

The residence time of the reaction solution in the microreactor, where appropriate in the microreactor and the residence zone, is preferably $\leq 15$ hours, particularly preferably $\leq 3$ hours, very particularly preferably $\leq 1$ hour.

The process according to the invention can be carried out in a very broad temperature range, which is essentially restricted by the heat resistance of the materials employed for the construction of the microreactor, any residence zone and further constituents, such as, for example, connections and seals, and by the physical properties of the solutions and/or liquids employed. The process according to the invention is preferably carried out at a temperature of from $-100$ to $+250°$ C., particularly preferably from $-78$ to $+150°$ C. and very particularly preferably from 0 to $+40°$ C.

The process according to the invention can be carried out either continuously or batchwise. It is preferably carried out continuously.

For carrying out the process according to the invention for the metathesis reaction of unsaturated organic compounds, it is necessary that the metathesis reaction be carried out as far as possible in the homogeneous liquid phase containing no or only very small solid particles since otherwise the channels present in the microreactors become blocked.

The course of the metathesis reaction in the process according to the invention can be followed using various analytical methods known to the person skilled in the art and regulated if necessary. The course of the reaction is preferably followed by chromatography, particularly preferably by gas chromatography and/or by high-pressure liquid chromatography and regulated if necessary. Control of the reaction in the process according to the invention is significantly improved compared with known processes.

After the reaction, the organic compounds formed are isolated if desired. The product(s) formed is (are) preferably isolated from the reaction mixture by extraction.

Unsaturated organic compounds which can be employed in the process according to the invention are all unsaturated organic compounds which are known to the person skilled in the art as substrates for metathesis reactions. The unsaturated organic compounds are preferably selected from aliphatic, aromatic or heteroaromatic alkenes.

Aliphatic alkenes which can be employed are all aliphatic alkenes which are known to the person skilled in the art and which are suitable as substrate for metathesis reactions. This also includes straight-chain and branched alkenes.

Aromatic alkenes which can be employed are all aromatic alkenes which are known to the person skilled in the art and which are suitable as substrate for metathesis reactions. For the purposes of the invention, this includes compounds and/or derivatives which have a monocyclic and/or polycyclic homoaromatic basic structure or a corresponding moiety, for example in the form of substituents.

Heteroaromatic alkenes which can be employed are all heteroaromatic alkenes which are known to the person skilled in the art, which are suitable as substrate for metathesis reactions and which contain at least one hetero atom. For the purposes of the invention, heteroaromatic compounds include heteroaromatic compounds and/or derivatives thereof which have at least one monocyclic and/or polycyclic heteroaromatic basic structure or a corresponding moiety, for example in the form of substituents. Heteroaromatic basic structures or moieties particularly preferably contain at least one oxygen, nitrogen or sulfur atom.

Metathesis catalysts which can be employed in the process according to the invention are all metathesis catalysts which are known to the person skilled in the art and which are suitable for metathesis reactions, or a mixture of at least two catalysts. Preferably, only one metathesis catalyst is in each case used in the process according to the invention.

In a further preferred embodiment, at least one metathesis catalyst selected from carbene or carbyne complexes or a mixture of these complexes, is employed.

In a particularly preferred embodiment, the carbene complex used is at least one complex selected from bis(tricyclohexylphosphine)benzylideneruthenium dichloride ($Cl_2(Cy_3P)_2Ru=CHPh$, "Grubbs" catalyst), a variant or derivative of the "Grubbs" catalyst, 2,6-diisopropylphenylimidoneophylidenemolybdenum bis(hexafluoro-tert-butoxide) ($2,6\text{-}iPr_2C_6H_3N=Mo\{OC(CF_3)_2Me\}_2=CHCMe_2Ph$, "Schrock" catalyst), a variant or derivative of the "Schrock" catalyst, or a mixture of the above-mentioned complexes.

In the process according to the invention, the molar ratio of unsaturated organic compound employed to metathesis catalyst employed depends on the reactivity of the unsaturated organic compounds employed and of the metathesis catalyst. The unsaturated organic compound and the metathesis catalyst are preferably used in an equimolar ratio. In another preferred embodiment, the unsaturated organic compound is employed in a molar excess of up to 10,000-fold, particularly preferably in a 10-fold to 100-fold excess, very particularly preferably in a 20-fold to 30-fold excess, relative to the metathesis catalyst.

The selectivity of the reaction depends, besides on the concentration of the reagents employed, on a number of further parameters, such as, for example, the temperature, the type of metathesis catalyst used or the residence time. It is possible for the person skilled in the art to match the various parameters to the respective metathesis reaction in such a way that the desired product(s) is (are) obtained.

It is essential for the process according to the invention that the unsaturated organic compounds and metathesis catalyst employed are either themselves liquid or are in dissolved form. If these compounds are not themselves already in liquid form, they must therefore be dissolved in a suitable solvent before the process according to the invention is carried out. Preferred solvents are water, halogenated solvents, particularly preferably dichloromethane, chloroform, 1,2-dichloroethane or 1,1,2,2-tetrachloroethane, straight-chain, branched or cyclic paraffins, particularly preferably pentane, hexane, heptane, octane, cyclopentane, cycloheptane or cyclooctane, or straight-chain, branched or cyclic ethers, particularly preferably diethyl ether, methyl tert-butyl ether, tetrahydrofuran or dioxane, aromatic solvents, particularly preferably toluene, xylenes, ligroin or phenyl ether, or mixtures of these solvents.

In the process according to the invention, the danger to people and the environment due to released chemicals is considerably reduced and thus results in increased safety during handling of hazardous materials. The metathesis reaction of unsaturated organic compounds by the process according to the invention furthermore enables better control of the reaction conditions, such as, for example, reaction duration and reaction temperature, than is possible in the conventional processes. The temperature can be selected individually and kept constant in each volume unit of the system. The course of the metathesis reaction in the reduction can be regulated very quickly and precisely in the process according to the invention. Protective-gas conditions can be achieved and maintained very easily. The organic products formed can thus be obtained in very good and reproducible yields.

It is also particularly advantageous that the process according to the invention can be carried out continuously. This makes it faster and less expensive compared with conventional processes, and it is possible to prepare any desired amounts of the desired organic compounds without major measurement and control effort.

The invention is explained below with reference to an example. This example serves merely to explain the invention and does not restrict the general inventive idea.

EXAMPLES

Ring-Closing Metathesis Reaction of 1,7-Octadiene to Cyclohexene

The ring-closing metathesis reaction of 1,7-octadiene with bis(tricyclohexylphosphine)benzylideneruthenium dichloride ("Grubbs" catalyst) was carried out in a static micromixer (Technical University of Ilmenau, Faculty of Machine Construction, Dr.-Ing. Norbert Schwesinger, PO Box 100565, D-98684, Ilmenau) having a physical size of 40mm×25 mm×1 mm and having a total of 11 mixing stages with a volume of 0.125 µl each. The total pressure loss was about 1000 Pa.

The static micromixer was connected via an outlet and an Omnifit medium-pressure HPLC connector (Omnifit, Great Britain) to a Teflon capillary having an internal diameter of 0.49 mm and a length of 5.0 m. The reaction was carried out at room temperature.

A 2 ml disposable injection syringe was filled with part of a solution of 110 mg (1 mmol) of 1,7-octadiene and 5 ml of dichloromethane, and a further 2 ml syringe was filled with part of a solution of 40 g (0.05 mmol) of bis (tricyclohexylphosphine)benzylideneruthenium dichloride ("Grubbs" catalyst) in 5 ml of dichloromethane. The contents of the two syringes were subsequently transferred into the static micromixer by means of a metering pump (Harvard Apparatus Inc., Pump 22, South Natick, Mass., USA). Before performance of the reaction, the experimental arrangement was calibrated with respect to the dependence of the residence time on the pump flow rate. The pump rate was set in such a way that a flow rate of 20 $\mu$l/min and thus a residence time of about 3.5 hours should result. Owing to the formation of gaseous ethene in the metathesis reaction, the residence time in the reactor and thus the reaction time was considerably shorter and was about 1 hour. The reactions were followed with the aid of a Merck Hitachi LaChrom HPLC instrument. At the end of the reaction, complete conversion of the 1,7-octadiene employed was established by means of a Hewlett-Packard GC-MS instrument. Besides small amounts of toluene, styrene and tricyclohexylphosphine, the only product found was cyclohexene.

What is claimed is:

1. Process for the metathesis reaction of unsaturated organic compounds comprising at least one unsaturated organic compound in liquid or dissolved form is mixed with at least one metathesis catalyst in liquid or dissolved form in at least one microreactor and reacted for a residence time, to form an organic compound which is optionally isolated from the reaction mixture, wherein the microreactor is a static micromixer, and wherein the total volume of reactants is less than 1000 $\mu$l, and the liquids in the reactor are vertically separated and subsequently rejoined in such a way so that a vertical boundary layer develops.

2. Process according to claim 1, wherein the microreactor is connected via an outlet to a capillary.

3. Process according to claim 1, wherein the volume of the microreactor is $\leq$100 $\mu$l.

4. Process according to claim 1, wherein the microreactor is heatable.

5. Process according to claim 1, wherein the microreactor has channels having a diameter of from 10 to 1000 $\mu$m.

6. Process according to claim 1, wherein the reaction mixture flows through the microreactor at a flow rate of from 0.01 $\mu$l/min to 100 ml/min.

7. Process according to claim 1, wherein the residence time of the compounds employed in the microreactor, and the capillaries, is $\leq$15.

8. Process according to claim 1, wherein it is carried out at a temperature of from −100 to +250° C.

9. Process according to claim 1, wherein the course of the reaction is monitored by chromatography and optionally regulated.

10. Process according to claim 1, wherein the unsaturated organic compounds are selected from aliphatic, aromatic or heteroaromatic alkenes.

11. Process according to claim 1, wherein at least one metathesis catalyst which is a carbene or carbine complex or a mixture thereof is used.

12. Process according to claim 11, wherein the carbine complex used is at least one bis(tricyclohexylphosphine)-benzylideneruthenium dichloride Grubbs catalyst 2,6-diisopropylphenylimido-neophylidenemolybdenum bis (hexafluoro-tert-butoxide or Schrock catalyst or a mixture thereof.

13. Process according to claim 1, wherein the unsaturated organic compound is employed in an equimolar ratio or a molar excess of up to 10,000-fold, relative to the metathesis catalyst.

14. Process according to claim 1, wherein the metathesis reaction is a ring-closing metathesis reaction of an unsaturated organic compound.

* * * * *